United States Patent
Narimatsu et al.

(10) Patent No.: US 6,669,645 B2
(45) Date of Patent: Dec. 30, 2003

(54) AUTONOMIC-NERVE-FUNCTION EVALUATING APPARATUS

(75) Inventors: Kiyoyuki Narimatsu, Komaki (JP); Toshihiko Ogura, Komaki (JP); Akira Tampo, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 10/269,880

(22) Filed: Oct. 15, 2002

(65) Prior Publication Data

US 2003/0158471 A1 Aug. 21, 2003

(30) Foreign Application Priority Data

Feb. 19, 2002 (JP) ......................................... 2002-041396

(51) Int. Cl.[7] .................................................. A61F 5/00
(52) U.S. Cl. ........................ 600/485; 600/481; 600/500; 600/490
(58) Field of Search ................................ 600/481, 485, 600/490, 492, 493–6, 500–503

(56) References Cited

U.S. PATENT DOCUMENTS

| 5,099,853 | A | | 3/1992 | Uemura et al. | |
| 5,797,840 | A | * | 8/1998 | Akselrod et al. | ............ 600/301 |
| 5,830,148 | A | * | 11/1998 | Inukai et al. | ................ 600/481 |
| 6,565,515 | B2 | * | 5/2003 | Ogura | .......................... 600/494 |

FOREIGN PATENT DOCUMENTS

| JP | U 60-83603 | 6/1985 |
| JP | A 5-200030 | 8/1993 |
| JP | B2 2592513 | 12/1996 |
| JP | B2 2798677 | 7/1998 |

* cited by examiner

Primary Examiner—Robert L. Nasser
(74) Attorney, Agent, or Firm—Oliff & Berridge, PLC (57) ABSTRACT

An apparatus for evaluating a function of an autonomic nerve of a living subject, including a heart-rate measuring device which iteratively measures a heart rate of the subject, a cuff-pressure changing device which changes a pressure in a first cuff adapted to be wound around an inferior limb of the subject, and a pressure in a second cuff adapted to be wound around a superior limb of the subject, so as to press the inferior and superior limbs, and a dispersion-degree determining device for determining a first degree of dispersion of the heart-rate values iteratively measured by the heart-rate measuring device after the cuff-pressure changing device starts pressing the inferior and superior limbs.

18 Claims, 8 Drawing Sheets

AUTONOMIC-NERVE-FUNCTION EVALUATING APPARATUS

BACKGROUND OF THE INVENTION

1. Field of the Invention

The present invention relates to an autonomic-nerve-function evaluating apparatus which can easily evaluate function or activity of autonomic nerve of a living subject.

2. Related Art Statement

When a person who has functional disorder of autonomic nerve, such as autonomic imbalance, stands up, the person may show, e.g., a symptom of orthostatic hypotension, i.e., a large blood-pressure decrease. When functional disorder of autonomic nerve, or orthostatic hypotension is diagnosed, a blood-pressure value of a patient is iteratively measured after the patient stands up from a lying position, and a trend of changing of the thus measured blood-pressure values is recorded on a recording medium. Concurrently, a position of the patient is iteratively detected, and the thus detected positions are also recorded on the recording medium. This autonomic-nerve evaluation is carried out by, e.g. the apparatus disclosed in Japanese Utility Model Document JITSU-KAI-SHO No. 60-83603 and Japanese Patent Document TOKU-KAI-HEI No. 5-200030.

The above-described, conventional autonomic-nerve-function evaluating apparatus requires the patient to take a special resting position for the purpose of reading only blood-pressure changes caused by the standing-up load, or needs to employ a considerably large mechanism for the purpose of tilting a bed on which the patient lies, from its horizontal position to its vertical position, and thereby applying the standing-up load to the patient. Thus, the conventional apparatus is not easy to use and accordingly it has not been widely used yet.

SUMMARY OF THE INVENTION

It is therefore an object of the present invention to provide an autonomic-nerve-function evaluating apparatus which can easily evaluate function of autonomic nerve of a living subject.

In the above-identified background, the Inventors have carried out extensive studies, and have found that when inferior and superior limbs of a living subject are pressed for, e.g., measuring respective blood-pressure values of the inferior and superior limbs and thereby measuring an inferior-and-superior-limb blood-pressure index of the subject, heart rate and pulse pressure of the subject are transitionally influenced or changed by the pressing. It is speculated that those changes are caused by the autonomic nerve of the subject that functions, responsive to the load temporarily applied to the circulatory organ of the subject, to cause the circulatory organ to positively send blood and thereby recover the flow of peripheral blood in the inferior and superior limbs. Thus, the Inventors have found that it is possible to evaluate or inspect activity of autonomic nerve of a living subject by utilizing the above-indicated phenomenon, i.e., by utilizing respective changes of heart rate and pulse pressure of the subject when inferior and superior limbs of the subject are pressed using cuffs to apply load to the circulatory organ of the subject, without needing to require the subject to take a special resting position or without needing to employ a considerably large-size mechanisms for tilting a bed on which the subject lies. The present invention has been developed based on these findings.

The above object has been achieved by the present invention. According to a first aspect of the present invention, there is provided an apparatus for evaluating a function of an autonomic nerve of a living subject, comprising a heart-rate measuring device which iteratively measures a heart rate of the subject; a cuff-pressure changing device which changes a pressure in a first cuff adapted to be wound around an inferior limb of the subject, and a pressure in a second cuff adapted to be wound around a superior limb of the subject, so as to press the inferior and superior limbs; and a dispersion-degree determining means for determining a first degree of dispersion of the heart-rate values iteratively measured by the heart-rate measuring device after the cuff-pressure changing device starts pressing the inferior and superior limbs.

According to this aspect, the dispersion-degree determining means determines the first degree of dispersion of the heart-rate values measured by the heart-rate measuring device after the cuff-pressure changing device starts pressing the inferior and superior limbs of the subject. Since the degree of dispersion of the heart-rate values indicates the activity of the function of the autonomic nerve of the subject, the function of the autonomic nerve can be easily evaluated based on the degree of dispersion of the heart-rate values, without needing to require the subject to take a special resting position or without needing to use a considerably large-size mechanism for tilting a bed on which the subject lies.

According to a preferred feature of the first aspect of the present invention, the dispersion-degree determining means determines a second degree of dispersion of the heart-rate values iteratively measured by the heart-rate measuring device before the cuff-pressure changing device starts pressing the inferior and superior limbs, and the apparatus further comprises an evaluating means for evaluating the function of the autonomic nerve of the subject based on a change of the first degree of dispersion from the second degree of dispersion.

According to this feature, the activity of the autonomic nerve of the subject can be evaluated based on an amount or rate of change of the first degree of dispersion of the heart-rate values measured after the pressing of the inferior and superior limbs of the subject, from the second degree of dispersion of the heart-rate values measured before the pressing. Thus, individual differences are removed and accordingly a very accurate evaluation can be made.

According to another feature of the first aspect of the present invention, the dispersion-degree determining means determines, as the first degree of dispersion, a variance of the heart-rate values iteratively measured by the heart-rate measuring device.

According to this feature, the function of the autonomic nerve can be easily evaluated based on the variance $\sigma_{HR}^2$ of the heart-rate values, without needing to require the subject to take a special resting position, or use a considerably large-size mechanism for tilting a bed on which the subject lies.

According to a second aspect of the present invention, there is provided an apparatus for evaluating a function of an autonomic nerve of a living subject, comprising a pulse-pressure measuring device which iteratively measures a pulse pressure of the subject; a cuff-pressure changing device which changes a pressure in a first cuff adapted to be wound around an inferior limb of the subject, and a pressure in a second cuff adapted to be wound around a superior limb of the subject, so as to press the inferior and superior limbs;

and a dispersion-degree determining means for determining a first degree of dispersion of the pulse-pressure values iteratively measured by the pulse-pressure measuring device after the cuff-pressure changing device starts pressing the inferior and superior limbs.

According to this aspect, the dispersion-degree determining means determines the first degree of dispersion of the pulse-pressure values measured by the pulse-pressure measuring device after the cuff-pressure changing device starts pressing the inferior and superior limbs of the subject. Since the degree of dispersion of the pulse-pressure values indicates the activity of the function of the autonomic nerve of the subject, the function of the autonomic nerve can be easily evaluated based on the degree of dispersion of the pulse-pressure values, without needing to require the subject to take a special resting position or use a considerably large-size mechanism for tilting a bed on which the subject lies.

According to a preferred feature of the second aspect of the present invention, the dispersion-degree determining means determines a second degree of dispersion of the pulse-pressure values iteratively measured by the pulse-pressure measuring device before the cuff-pressure changing device starts pressing the inferior and superior limbs, and wherein the apparatus further comprises an evaluating means for evaluating the function of the autonomic nerve of the subject based on a change of the first degree of dispersion from the second degree of dispersion.

According to this feature, the activity of the autonomic nerve of the subject can be evaluated based on an amount or rate of change of the first degree of dispersion of the pulse-pressure values measured after the pressing of the inferior and superior limbs of the subject, from the second degree of dispersion of the pulse-pressure values measured before the pressing. Thus, individual differences are removed and accordingly a very accurate evaluation can be made.

According to another feature of the second aspect of the present invention, the dispersion-degree determining means determines, as the first degree of dispersion, a variance of the pulse-pressure values iteratively measured by the pulse-pressure measuring device.

According to this feature, the function of the autonomic nerve can be easily evaluated based on the variance $\sigma_{PP}^2$ of the pulse-pressure values, without needing to require the subject to take a special resting position, or use a considerably large-size mechanism for tilting a bed on which the subject lies.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
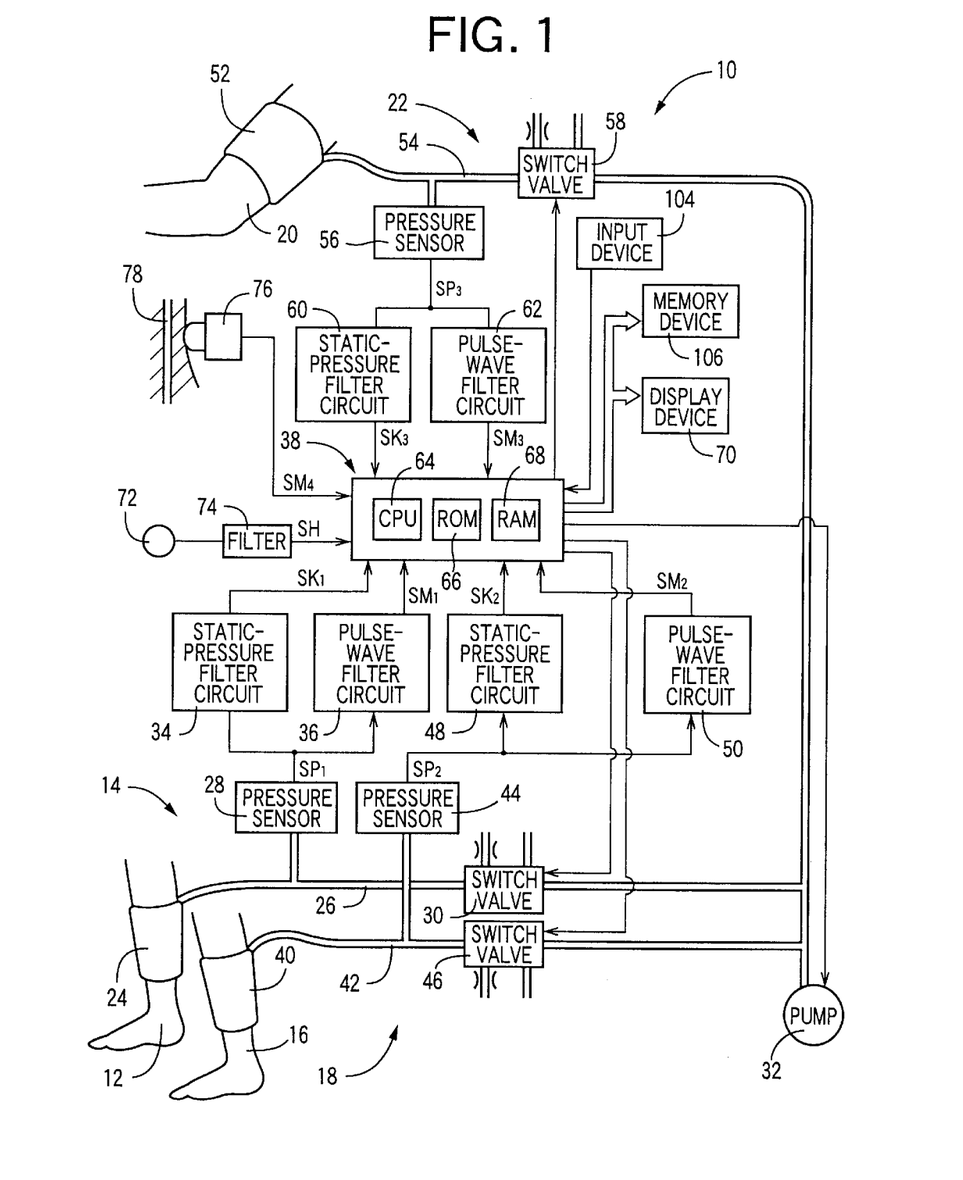
FIG. 1 is a diagrammatic view for explaining a construction of an inferior-and-superior-limb blood-pressure-index measuring apparatus which has the function of evaluating function of autonomic nerve and to which the present invention is applied.

Hereinafter, there will be described an embodiment of the present invention in detail by reference to the drawings. FIG. 1 is a diagrammatic view for explaining a construction of an inferior-and-superior-limb blood-pressure-index measuring apparatus 10 which has the function of evaluating function of autonomic nerve of a living subject and to which the present invention is applied. In the present apparatus 10, ankles are selected as inferior limbs and an upper arm is selected as a superior limb. The present apparatus 10 carries out measurements on a patient as a living subject who takes a face-down, a lateral, or a face-up position so that an upper arm and ankles of the patient are substantially level with one another.

In FIG. 1, the inferior-and-superior-limb blood-pressure-index measuring apparatus 10 includes a right-leg first blood-pressure measuring device 14 which measures a blood-pressure value of a right ankle 12 of the patient, a left-leg first blood-pressure measuring device 18 which measures a blood-pressure value of a left ankle 16 of the patient, and a second blood-pressure measuring device 22 which measures a blood-pressure value of an upper arm 20 of the patient.

The right-leg first blood-pressure measuring device 14 includes an inflatable cuff 24 which includes a belt-like cloth bag and a rubber bag accommodated in the cloth bag and which is adapted to be wound around the right ankle 12 of the patient; a piping 26; and a pressure sensor 28, a switch valve 30, and an air pump 32 which are connected to the cuff 24 via the piping 26. The switch valve 30 is selectively placed in one of three positions, that is, a pressure-supply position in which the switch valve 30 allows a pressurized air to be supplied from the air pump 32 to the cuff 24; a slow-deflation position in which the switch valve 30 allows the pressurized air to be slowly discharged from the cuff 24; and a quick-deflation position in which the switch valve 30 allows the pressurized air to be quickly discharged from the cuff 24.

The pressure sensor 28 detects an air pressure in the cuff 24, and supplies a pressure signal, $SP_1$, representing the detected air pressure, to a static-pressure filter circuit 34 and a pulse-wave filter circuit 36. The static-pressure filter circuit 34 includes a low-pass filter which extracts, from the pressure signal $SP_1$, a cuff-pressure signal, $SK_1$, representing a cuff pressure, $P_{C1}$, as a static component of the detected air pressure. The filter circuit 34 supplies the cuff-pressure signal $SK_1$ to a control device 38 via an analog-to-digital (A/D) converter, not shown.

The pulse-wave filter circuit 36 includes a band-pass filter which extracts, from the pressure signal $SP_1$, a pulse-wave signal, $SM_1$, representing a pulse wave as an oscillatory component of the detected air pressure that has prescribed frequencies. The filter circuit 36 supplies the pulse-wave signal $SM_1$ to the control device 38 via an A/D converter, not shown.

The left-leg first blood-pressure measuring device 18 includes an inflatable cuff 40, a piping 42, a pressure sensor 44, and a switch valve 46 which have respective constructions identical with those of the counterparts 24, 26, 28, 30 of the right-leg first blood-pressure measuring device 14. The switch valve 46 is connected to the air pump 32. The pressure sensor 44 detects an air pressure in the cuff 40, and supplies a pressure signal, $SP_2$, representing the detected air pressure, to a static-pressure filter circuit 48 and a pulse-wave filter circuit 50 which have respective constructions identical with those of the counterparts 34, 36 of the right-leg first blood-pressure measuring device 14. The static-pressure filter circuit 48 extracts, from the pressure signal $SP_2$, a cuff-pressure signal, $SK_2$, representing a cuff pressure, $P_{C2}$, as a static component of the detected air pressure, and supplies the cuff-pressure signal $SK_2$ to the control device 38 via an A/D converter, not shown. The pulse-wave filter circuit 50 extracts, from the pressure signal $SP_2$, a pulse-wave signal, $SM_2$, representing a pulse wave as an oscillatory component of the detected air pressure that has prescribed frequencies, and supplies the pulse-wave signal $SM_2$ to the control device 38 via an A/D converter, not shown.

The second blood-pressure measuring device 22 includes an inflatable cuff 52 which has a construction identical with the cuff 24 or 40 and which is adapted to be wound around the upper arm 20 (e.g., right upper arm) of the patient; and a piping 54, a pressure sensor 56, and a switch valve 58 which have respective constructions identical with those of the counterparts 26, 28, 30 of the right-leg first blood-pressure measuring device 14. The switch valve 58 is connected to the air pump 32. The pressure sensor 56 detects an air pressure in the cuff 52, and supplies a pressure signal, $SP_3$, representing the detected air pressure, to a static-pressure filter circuit 60 and a pulse-wave filter circuit 62 which have respective constructions identical with those of the counterparts 34, 36 of the right-leg first blood-pressure measuring device 14. The static-pressure filter circuit 60 extracts, from the pressure signal $SP_3$, a cuff-pressure signal, $SK_3$, representing a cuff pressure, $P_{C3}$, as a static component of the detected air pressure, and supplies the cuff-pressure signal $SK_3$ to the control device 38 via an A/D converter, not shown. The pulse-wave filter circuit 62 extracts, from the pressure signal $SP_3$, a pulse-wave signal, $SM_3$, representing a pulse wave as an oscillatory component of the detected air pressure that has prescribed frequencies, and supplies the pulse-wave signal $SM_3$ to the control device 38 via an A/D converter, not shown.

The control device 38 is essentially provided by a microcomputer including a CPU (central processing unit) 64, a ROM (read only memory) 66, a RAM (random access memory) 68, and an I/O (input-and-output) port, not shown, and processes input signals according to the control programs pre-stored in the ROM 66, while utilizing the temporary-storage function of the RAM 68. The control device 38 outputs, from the I/O port, drive signals to the air pump 32 and the three switch valves 30, 46, 58 to control the respective operations thereof, and additionally outputs display signals to a display device 70 to control what is displayed thereby.

A microphone 72 is attached, with an adhesive tape, not shown, to the skin of central portion of the chest of the patient, more specifically described, a prescribed heart-sound detecting position right above the apex cordis, the left end of the fourth intercostal sternum, the left end of the second intercostal sternum, the right end of the second intercostal sternum, or the right end of the fourth intercostal sternum. The microphone 72 detects heart sounds which are transmitted from the heart to the skin of the prescribed heart-sound detecting position. The heart sounds are produced when the heart starts outputting blood to the aorta, and when the heart ends outputting blood to the aorta. Thus, the heart sounds provide a pulse wave which is produced from the most upstream portion of the aorta. The microphone 72 functions as a first pulse-wave detecting device.

Figure 5:
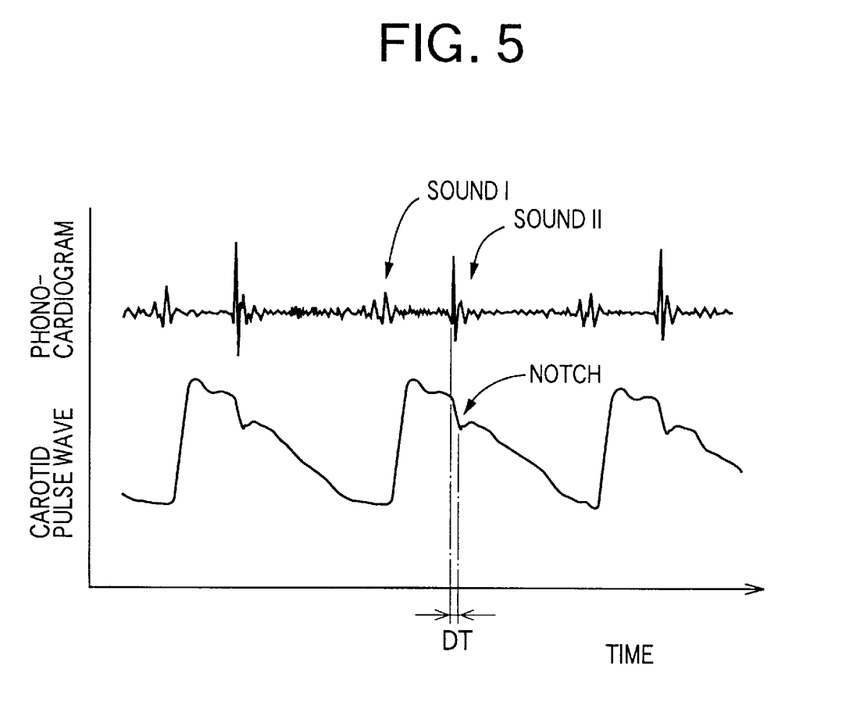
FIG. 5 is a graph showing respective examples of a phonocardiogram detected by a microphone of the apparatus of FIG. 1, and a carotid pulse wave detected by the carotid-pulse-wave sensor of the same apparatus.

The microphone 72 includes a piezoelectric element, not shown, which converts the sounds detected thereby into an electric signal, i.e., a heart-sound signal, SH, and outputs the heart-sound signal SH, which subsequently is amplified by a preamplifier, not shown, and is supplied to a filter device 74. Then, the signal SH is supplied to the control device 38 via a main amplifier and an A/D converter, both not shown. The filter device 74 includes four sorts of filters, not shown, which can be so selected and used that the low-pitched-sound components of the heart-sound signal SH are attenuated and the high-pitched-sound components of the same SH are exaggerated and accordingly the heart sounds can be easily heard by the auditory sense of a human being. An upper half portion of FIG. 5 shows an example of a phonocardiogram detected by the microphone 72. The phonocardiogram includes a first sound I corresponding to the closing of the mitral valve and the opening of the aortic valve, and a second sound II corresponding to the closing of the aortic valve.

A carotid-pulse-wave sensor 76 functions as a second pulse-wave detecting device which is worn on a portion of the patient that is located on a downstream side of the microphone 72 as the first pulse-wave detecting device, as seen in the direction of flowing of blood in the body of the patient, and which detects a pulse wave propagating through an artery running in that portion of the patient. The carotid-pulse-wave sensor 76 includes a contact member, and a vibration sensor, not shown, which detects vibration of the contact member. The carotid-pulse-wave sensor 76 is attached to a neck portion of the patient such that the contact member of the sensor 76 is held in pressed contact with skin right above a carotid artery 78 and detects a carotid pulse wave produced from the carotid artery 78. The carotid-pulse-wave sensor 76 supplies a carotid-pulse-wave signal, $SM_4$, representing the detected carotid pulse wave, to the control device 38 via an A/D converter, not shown. A lower half portion of FIG. 5 shows an example of the carotid pulse wave detected by the carotid-pulse-wave sensor 76. Since the carotid artery 78 has a considerably great diameter and is directly connected to the aorta, the waveform of the carotid pulse wave is substantially identical with that of an aortic pulse wave produced from the aorta.

Figure 2:
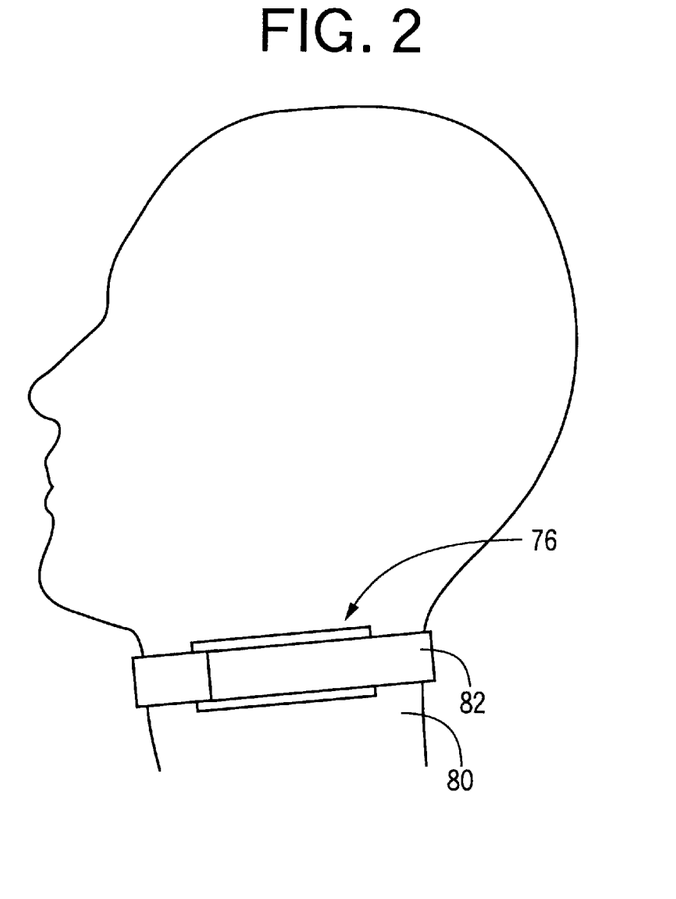
FIG. 2 is a view showing a state in which a carotid-pulse-wave sensor shown in FIG. 1 is worn.
Figure 3:
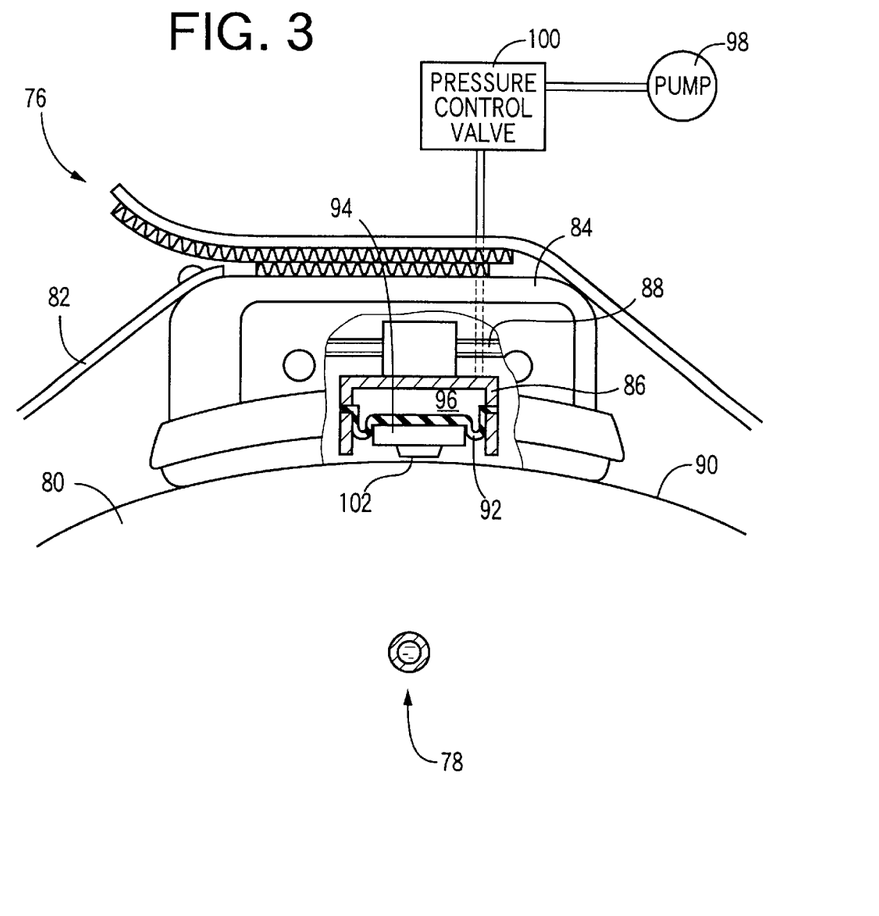
FIG. 3 is an elevation view for explaining a construction of the carotid-pulse-wave sensor of FIG. 1, a portion of the sensor being cut away.
Figure 4:
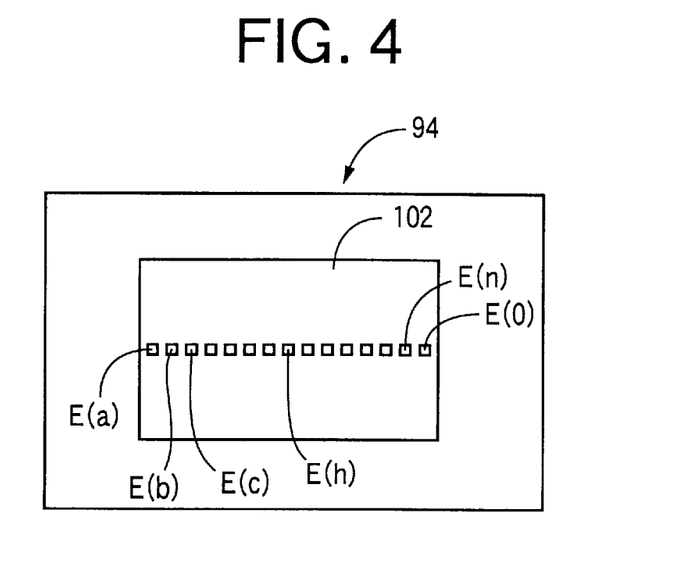
FIG. 4 is a view showing a press surface of a sensor element of the carotid-pulse-wave sensor shown in FIGS. 2 and 3.

The carotid-pulse-wave sensor 76 is worn on a neck portion 80 of the subject, as illustrated in FIG. 2, with the help of a band 82. As illustrated in detail in FIG. 3, the carotid-pulse-wave sensor 76 includes a container-like sensor housing 86; a case 84 which accommodates the sensor housing 86; and a feed screw 88 which is threadedly engaged with the sensor housing 82 and is rotated by an electric motor, not shown, provided in the case 84 so as to move the sensor housing 82 in a widthwise direction of the carotid artery 78. With the help of the band 82, the carotidpulse-wave sensor 76 is detachably attached to the neck portion 80, such that an open end of the sensor housing 86 is opposed to a body surface 90 of the neck portion 80. In addition, the carotid-pulse-wave sensor 76 includes a sensor element 94 which is secured via a diaphragm 92 to an inner wall of the sensor housing 86, such that the sensor element 54 is movable relative to the housing 86 and is advanceable out of the open end of the same 862. The sensor housing 86, the diaphragm 92, etc. cooperate with one another to define a pressure chamber 96, which is supplied with a pressurized air from an air pump 98 via a pressure-control valve 100, so that the sensor element 54 is pressed against the body surface 90 with a pressing force corresponding to the air pressure in the pressure chamber 96. The sensor housing 86 and the diaphragm 92 cooperate with each other to provide a pressing device which presses the sensor element 94 against the carotid artery 78, and the feed screw 88 and the not-shown motor cooperate with each other to provide a widthwise-direction moving device which moves the sensor element 94 in the widthwise direction of the carotid artery 78 and thereby changes a pressing position where the sensor element 54 is pressed on the body surface 90. The sensor element 54 has a pressing surface 102, and a number of semiconductor pressure-sensing elements (hereinafter, referred to as the "pressure-sensing elements") E which are arranged in the pressing surface 102 at a regular interval in the widthwise direction of the carotid artery 78, i.e., in the direction of movement of the sensor element 94 parallel to the feed screw 88, over a length greater than the diameter of the carotid artery 78. For example, as shown in FIG. 4, fifteen pressure-sensing elements E(a), E(b), . . . , E(o) are arranged at a regular interval of, e.g., 0.6 mm.

The carotid-pulse-wave sensor 76, constructed as described above, is pressed, with a pre-set optimum pressing force, against the body surface 90 of the neck portion 80 right above the carotid artery 78, so that the sensor element 94 detects a pressure pulse wave (i.e., a carotid pulse wave, wc) which is produced from the carotid artery 78 and is transmitted to the body surface 90, and supplies a pressure-pulse-wave signal $SM_4$ representing the detected carotid pulse wave wc, to the control device 32 via an A/D converter, not shown. In the lower half portion of FIG. 5, an example of the pressure-pulse-wave signal $SM_4$ continuously supplied from the sensor element 94, i.e., the carotid pulse wave wc, is indicated at solid line. The pressure pulse wave produced from the carotid artery 78 is calibrated based on the systolic and diastolic blood-pressure values measured by the second blood-pressure measuring device 22 including the cuff 52, so that the pressure pulse wave represents the blood pressure changing in the carotid artery 78. For example, an upper peak (a peak of a hill) of the pressure pulse wave represents a systolic blood pressure, and a lower peak (a bottom of a valley) of the pulse wave represents a diastolic blood pressure.

An input device 104 includes a keyboard, not shown, which is operated by an operator such as a doctor or a nurse to input an ID (identification) number identifying each patient. The input device 104 supplies, to the control device 38, a signal representing the ID number that has been inputted and identified by an identifying means 124. A memory device 106 may be provided by any one of well-known memory devices, such as a magnetic disk, a magnetic tape, a volatile semiconductor memory, or a non-volatile semiconductor memory. In addition, the memory device 106 stores, in respective prescribed memory areas thereof, an ankle-and-upper-arm blood-pressure index (AAI) and pulse-wave-propagation-velocity-related information.

Figure 6:
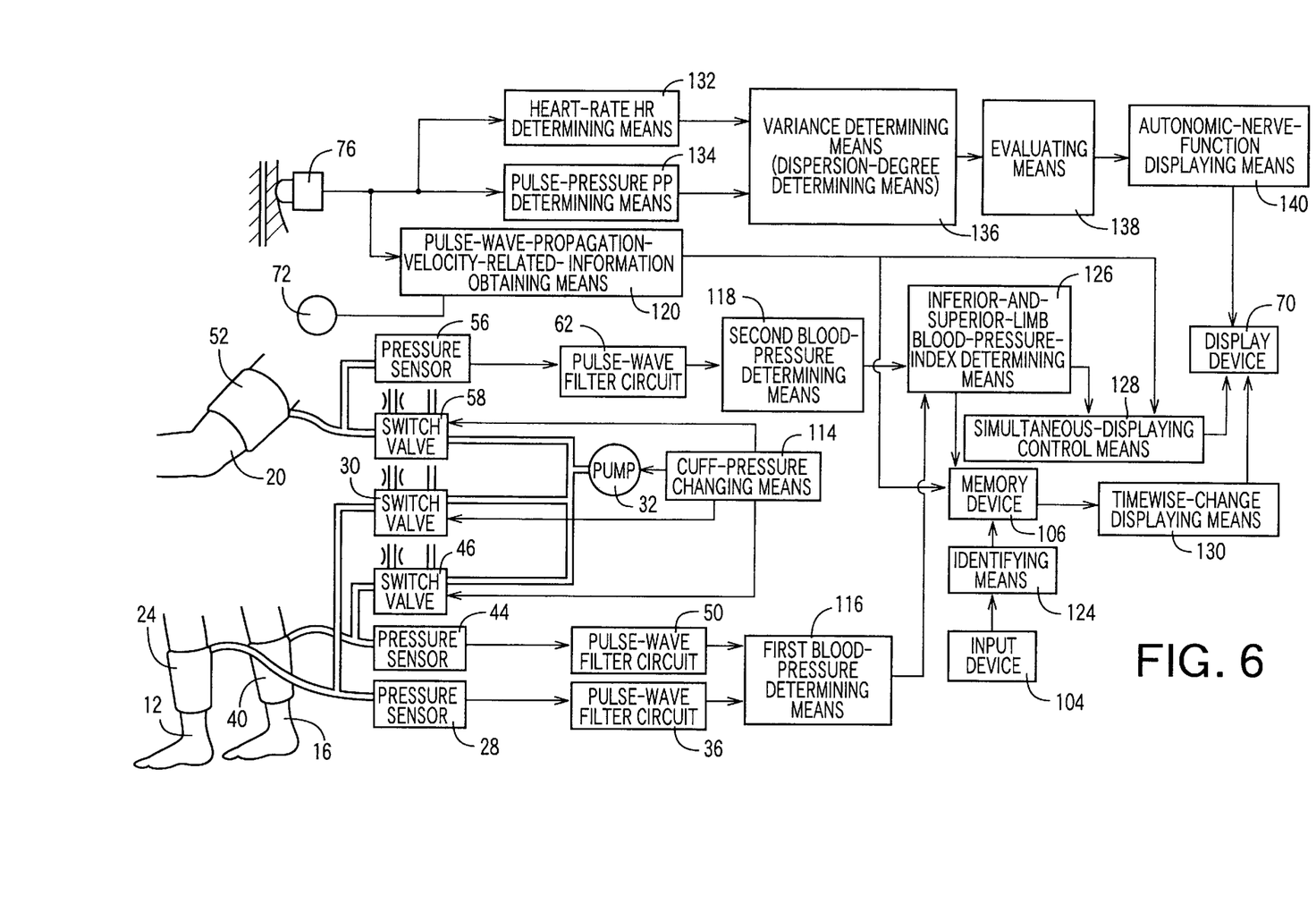
FIG. 6 is a diagrammatic view for explaining essential control functions of an electronic control device of the apparatus of FIG. 1.
Figure 7:
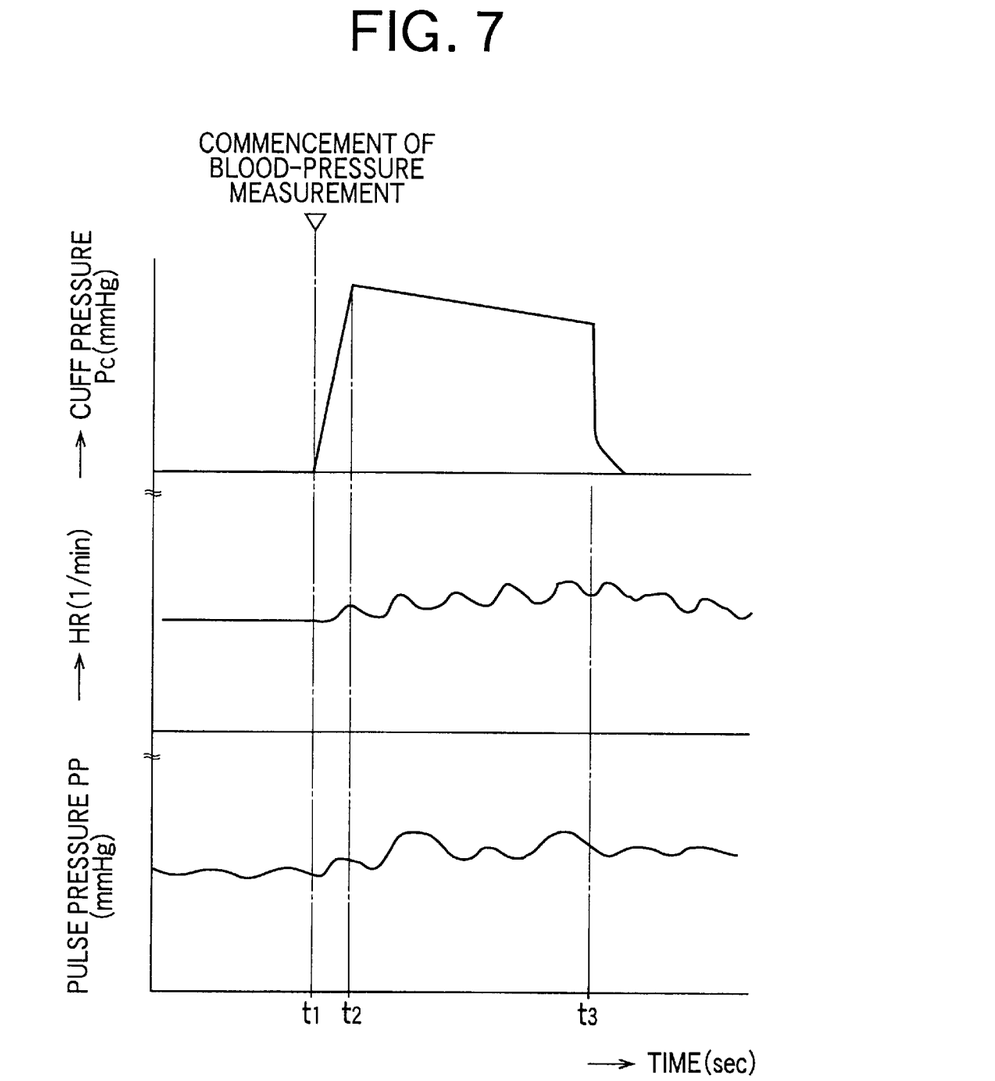
FIG. 7 is a graph showing respective changes of heart rate and pulse pressure of a living subject when limbs of the subject are pressed by cuffs and accordingly circulatory organ of the subject is subjected to load.

FIG. 6 is a diagrammatic view for explaining essential control functions of the control device 38. A cuff-pressure changing means 114 controls the air pump 32 and the three switch valves 30, 46, 58 each connected to the pump 32, such that the respective pressures of the three cuffs 24, 40, 52 are quickly increased up to a predetermined target pressure value, $P_{CM}$, (e.g., 180 mmHg) and then are slowly decreased at a rate of about 3 mmHg/sec. After the blood-pressure measuring operation has completed, the respective pressures of the three cuffs 24, 40, 52 are quickly decreased down to an atmospheric pressure. In FIG. 7, a time point, t1, indicates a quick-pressure-increase starting point when the quick increasing of respective pressures of the three cuffs 24, 40, 52 is started; a time point, t2, indicates a quick-pressure-increase ending point, i.e., a slow-pressure-decrease starting point; and a time point, t3, indicates a quick-pressure-decrease starting point.

A first blood-pressure determining means 116 determines right-leg first blood-pressure values, $BP1_R$, that is, blood-pressure values of the right ankle 12, according to well-known oscillometric method, based on the change of respective amplitudes of heartbeat-synchronous pulses of the pulse-wave signal $SM_1$ detected one by one during the slow decreasing of the pressure of the cuff 24 wound around the right ankle 12 under the control of the cuff-pressure changing means 114. In addition, the first blood-pressure determining means 116 determines left-leg first blood-pressure values, $BP1_L$, that is, blood-pressure values of the left ankle 16, according to the oscillometric method, based on the change of respective amplitudes of heartbeat-synchronous pulses of the pulse-wave signal $SM_2$ detected one by one during the slow decreasing of the pressure of the cuff 40 wound around the left ankle 16 under the control of the cuff-pressure changing means 114. The right-leg first blood-pressure values $BP1_R$ include a systolic blood-pressure value $BP1_{RSYS}$ and a diastolic blood-pressure value $BP1_{RDIA}$, and the left-leg first blood-pressure values $BP1_L$ include a systolic BP value $BP1_{LSYS}$ and a diastolic BP value $BP1_{LDIA}$. Hereinafter, when it is not needed to distinguish the right-leg first blood-pressure values BP1R and the left-leg first blood-pressure values BP1L from each other, those blood-pressure values as a whole will be referred to as the first blood-pressure values BP1.

A second blood-pressure determining means 118 determines second blood-pressure values, BP2, (e.g., systolic blood-pressure value $BP2_{SYS}$ and diastolic blood-pressure value $BP2_{DIA}$), that is, blood-pressure values of the upper arm 20, according to the well-known oscillometric method, based on the change of respective amplitudes of heartbeat-synchronous pulses of the pulse-wave signal $SM_3$ detected one by one during the slow decreasing of the pressure of the cuff 52 wound around the upper arm 20 under the control of the cuff-pressure changing means 114.

A pulse-wave-propagation-velocity-related-information obtaining means 120 iteratively obtains pulse-wave-propagation-velocity-related information that is related to a velocity at which a pulse wave propagates, based on a time difference between a time of occurrence of a prescribed periodic point of the first pulse wave detected by the first pulse-wave detecting device and a time of occurrence of a prescribed periodic point of the second pulse wave detected by the second pulse-wave detecting device. For example, the information obtaining means 120 includes a time-difference determining means for iteratively determining a time difference (i.e., a pulse-wave propagation time), DT, shown in FIG. 5, i.e., a time difference between a time point when the microphone 72 detects a starting point of a second heart sound II (this point corresponds to a notch of an aortic pulse wave where the amplitude thereof ends decreasing and starts increasing), and a time point when the carotid-pulse-wave sensor 76 detects a notch of the carotid pulse wave. In addition, the information obtaining means 120 iteratively determines, based on each time difference DT iteratively determined by the time-difference determining means, a pulse-wave propagation velocity, PWV (m/sec), at which a pulse wave propagates in an artery of the subject, according to the following Expression 1, pre-stored in the ROM 66:

$$PWV=L/DT \qquad (1)$$

In the above Expression 1, L (m) is a distance from the left ventricle, via the aorta, to the position where the carotid-pulse-wave sensor 76 is worn, and is replaced with a default value that is experimentally determined in advance.

A superior-and-inferior-limb blood-pressure-index determining means 126 determines an ankle-and-upper-arm (inferior-and-superior-limb) blood-pressure index (i.e., Ankle/Brachium Blood Pressure index; hereinafter, referred to as ABI) based on one of the first blood-pressure values BP1 determined by the first blood-pressure determining means 116, and a corresponding one of the second blood-pressure values BP2 determined by the second blood-pressure determining means 118 (for example, the second systolic BP value $BP2_{SYS}$ corresponds to the first systolic BP value $BP1_{SYS}$). The index value ABI may be determined by dividing the first blood-pressure value BP1 by the second blood-pressure value BP2, or dividing the second blood-pressure value BP2 by the first blood-pressure value BP1. The thus determined index value ABI is stored in the memory device 106.

A simultaneous-displaying control means 128 controls the display device 70 to simultaneously display the pulse-wave-propagation-velocity-related information obtained by the pulse-wave-propagation-velocity-related information obtaining means 120 and the index value ABI determined by the ankle-and-upper-arm blood-pressure-index determining means 126. For example, the display device 70 simultaneously displays the pulse-wave-propagation-velocity-related information (in digits) and the index value ABI (in digits), side by side. Alternatively, the display device 70 displays, in a two-dimensional screen thereof that is defined by a first axis indicative of ankle-and-upper-arm blood-pressure index and a second axis indicative of pulse-wave-propagation-velocity-related information, a mark or a symbol at a position corresponding to the actually determined index value ABI and the actually obtained pulse-wave-propagation-velocity-related information.

A timewise-change displaying means 130 operates the display device 70 to display, in a two-dimensional plane, not only the symbol, displayed by the simultaneous-displaying control means 128, that represents the current index value ABI and the current pulse-wave-propagation-velocity-related information, but also one or more symbols at one or more positions corresponding to one or more past ABI values and one or more past pieces of pulse-wave-propagation-velocity-related information that had been obtained from the current patient and have been stored in the memory device 106. The one or more past pieces of pulse-wave-propagation-velocity-related information are pieces of information that were obtained when the one or more past ABI values were obtained, respectively. The one or more symbols representing the one or more past values and pieces of information may be identical with the symbol representing the current value and information, but it is preferred that the former symbols differ from the latter symbol so as to be distinguished from the latter symbol.

A heart-rate determining means 132 iteratively determines a heart rate, HR (1/min), of the subject, i.e., a number of heartbeats per minute, based on a time period between each pair of successive heartbeat-synchronous pulses of the carotid pulse wave continuously detected by the carotid-pulse-wave sensor 76. A pulse-pressure determining means 134 iteratively determines a pulse pressure, PP (mmHg), of the subject, i.e., a difference between the greatest magnitude (i.e., a systolic blood pressure) and the smallest magnitude (i.e., a diastolic blood pressure) of each of successive heartbeat-synchronous pulses of the carotid pulse wave, i.e., an amplitude of the each heartbeat-synchronous pulse of the pulse wave, based on a waveform of the each pulse of the pulse wave detected by the carotid-pulse-wave sensor 76.

Before the cuffs 24, 40, 52 press the respective portions of the subject, the heart-rate values HR of the subject do not change basically. However, after the cuffs 24, 40, 52 starts pressing the ankles 12, 16 and the upper arm 20, the flow of peripheral blood is blocked or restrained, so that load is applied to the circulatory organ of the subject. Consequently, as shown in FIG. 7, the autonomic nerve of the subject functions to recover the flow of peripheral blood, thereby producing fluctuations of the heart-rate values HR. In addition, before the cuffs 24, 40, 52 press the respective portions of the subject, the pulse-pressure values PP show small fluctuations having a constant amplitude and a period equal to the period of respiration. However, after the cuffs 24, 40, 52 starts pressing the ankles 12, 16 and the upper arm 20, the flow of peripheral blood is blocked or restrained, so that load is applied to the circulatory organ of the subject. Consequently, as shown in FIG. 7, the autonomic nerve of the subject functions to recover the flow of peripheral blood, thereby producing random fluctuations of the pulse-pressure values PP. A variance determining means 136, described below, quantitatively determines a degree of dispersion of the heart-rate values HR measured, and a degree of dispersion of the pulse-pressure values PP measured, when load is applied to the circulatory organ of the subject.

The variance determining means 136 functions as a sort of dispersion-degree determining means. The variance determining means 136 determines, as a degree of dispersion, a variance of each of (a) the heart-rate values HR and (b) the pulse-pressure values PP that are iteratively measured during a prescribed period of from several tens of seconds to several minutes after the pressing of the upper arm 20 with the cuff 52 and the pressing of the ankles 12, 16 with the cuffs 24, 40 under the control of the cuff-pressure changing means 114 are simultaneously started to measure respective blood-pressure values of the upper arm 20 and the ankles 12, 16 and thereby measure an index value ABI. For example, providing that the heart-rate values HR iteratively measured are $x_1, x_2, x_3, \ldots, x_N$, the variance determining means 136 determines a variance, $\sigma_{HR}^2$, of the heart-rate values HR according to the following Expression 2 and, providing that the pulse-pressure values PP iteratively measured are $y_1, y_2, y_3, \ldots, y_N$, the variance determining means 136 determines a variance, $\sigma_{PP}^2$, of the pulse-pressure values PP according to the following Expression 3:

$$\sigma_{HR}^2 = \Sigma(x_i - x_{AV})^2/N \qquad (2)$$

where $x_{AV}$ is an average of $x_1$ to $x_N$.

$$\sigma_{PP}^2 = \Sigma(y_i - y_{AV})^2/N \qquad (3)$$

where $y_{AV}$ is an average of $y_1$ to $y_N$.

An evaluating means 138 evaluates a function of the autonomic nerve of the subject, based on an amount or rate of change of the degree of dispersion, e.g., the variance $\sigma_{HR}^2$, determined by the variance determining means 136 based on the heart-rate values HR iteratively measured after the upper arm and the ankles are simultaneously pressed by the cuff-pressure changing means 114, from a degree of dispersion determined by the variance determining means 136 based on heart-rate values HR iteratively measured before the upper arm and the ankles are simultaneously pressed, and/or an amount or rate of change of the degree of dispersion, e.g., the variance $\sigma_{PP}^2$, determined by the variance determining means 136 based on the pulse-pressure values PP iteratively measured after the upper arm and the ankles are simultaneously pressed by the cuff-pressure changing means 114, from a degree of dispersion determined by the variance determining means 136 based on pulse-pressure values PP iteratively measured before the upper arm and the ankles are simultaneously pressed. For example, the evaluating means 138 evaluates the function of the autonomic nerve in such a manner that the greater the amount or rate of change of the degree of dispersion, e.g., the variance $\sigma_{HR}^2$, of the heart-rate values HR is and/or the greater the amount or rate of change of the degree of dispersion, e.g., the variance $\sigma_{PP}^2$, of the pulse-pressure values PP is, the higher the function of the autonomic nerve is, and vice versa. The evaluation that the function of the autonomic nerve is low supports a diagnosis that the subject suffers autonomic imbalance.

An autonomic-nerve-function displaying means 140 operates the display device 70 to display the result of evaluation made by the evaluating means 138, e.g., a degree of function of the autonomic nerve, in the form of a digital value such as a numerical value, an analogue value such as a bar graph, or a selected one of several pre-set messages corresponding to several degrees.

Figure 8:
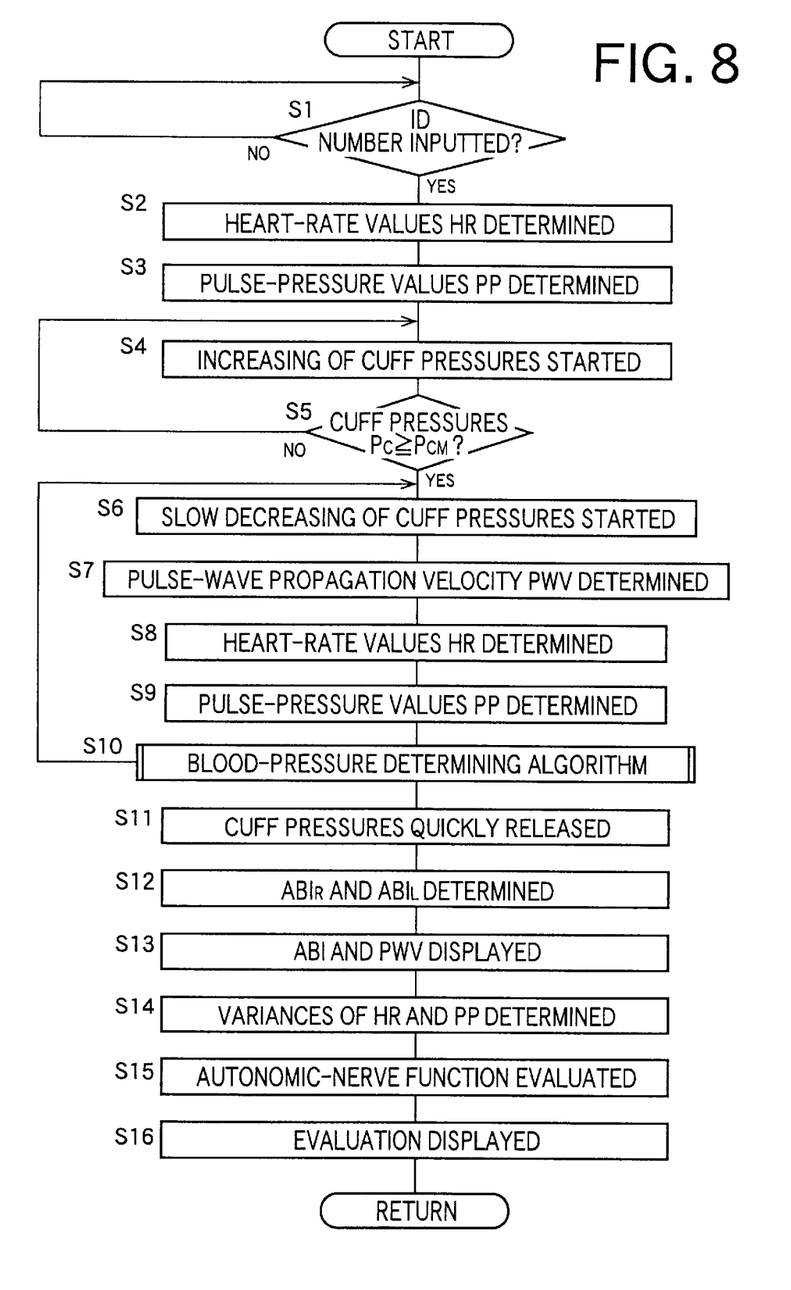
FIG. 8 is a flow chart representing a control program according to which the control device of the apparatus of FIG. 1 is operated.

FIG. 8 is a flow chart representing a control program according to which the control device 38 is operated. In the flow chart of FIG. 8, first, the control device 38 carries out Step S1 (hereinafter, "Step(s)" is omitted) corresponding to the identifying means 124. At S1, the control device judges whether an ID number identifying a current patient has been inputted through the input device 104, and is identical with one that has been registered in the control device. S1 is repeated until a positive judgment is made. Meanwhile, if a positive judgment is made at S1, the control goes to S2 corresponding to the heart-rate determining means 132. At S2, the control device determines a heart rate HR (1/min) of the subject, i.e., a number of heartbeats per minute, based on each of heartbeat-synchronous pulses of the carotid pulse wave continuously detected by the carotid-pulse-wave sensor 76. Then, the control goes to S3 corresponding to the pulse-pressure determining means 134. At S3, the control device determines a pulse pressure PP (mmHg), i.e., a difference between the greatest magnitude (a systolic blood pressure) and the smallest magnitude (a diastolic blood pressure) of each of the heartbeat-synchronous pulses of the carotid pulse wave, in other words, an amplitude of the each heartbeat-synchronous pulse, based on a waveform of the each heartbeat-synchronous pulse of the carotid pulse wave continuously detected by the carotid-pulse-wave sensor 76. The thus determined heart-rate values HR and pulse-pressure values PP are stored, in the memory device 106, as the values obtained before the pressing using the cuffs is started, i.e., before the load is applied to the circulatory organ of the subject.

Next, the control goes to S4 to S6 corresponding to the cuff-pressure changing means 114, for measuring blood-pressure values and thereby measuring an inferior-and-superior-limb blood-pressure index ABI. First, at S4, the three switch valves 30, 46, 58 are switched to their pressure-supply positions and the air pump 32 is operated, so that the respective pressures of the three cuffs 24, 40, 52 are quickly increased to press the ankles 12, 16 and the upper arm 20. At S5, the control device judges whether the pressure $P_C$ of each of the three cuffs 24, 40, 52 has reached a prescribed target pressure value $P_{CM}$, e.g., 180 mmHg, that would be higher than a systolic blood pressure of the patient. If a negative judgment is made at S5, S4 and S5 are repeated to continue increasing the pressures $P_C$ of the cuffs 24, 40, 52.

If a positive judgment is made at S5, the control goes to S6 to stop the air pump 32 and switch the switch valves 30, 46, 58 to their slow-deflation positions, so that the pressure $P_C$ of each cuff is slowly decreased at a prescribed low rate of about 3 mmHg/sec.

Then, at S7 corresponding to the pulse-wave-propagation-velocity-related-information obtaining means 120, the control device determines, as illustrated in FIG. 5, a pulse-wave propagation time DT as a time difference between a time when a starting point of a second heart sound II occurs to the heart-sound signal SH continuously supplied from the microphone 72, and a time when a notch occurs to the carotid-pulse-wave signal $SM_4$ continuously supplied from the carotid-pulse-wave sensor 76, that is, a time period needed for a pulse wave to propagate from the heart to the position where the sensor 76 is worn. In addition, the control device determines, upon each heartbeat of the patient, a pulse-wave propagation velocity PWV by substituting the thus determined pulse-wave propagation time DT for the above-indicated Expression 1. Then, the control goes to S8 corresponding to the heart-rate determining means 132. At S8, the control device determines a heart rate HR (1/min) of the subject, i.e., a number of heartbeats per minute, based on each heartbeat-synchronous pulse of the carotid pulse wave continuously detected by the carotid-pulse-wave sensor 76. Then, the control goes to S9 corresponding to the pulse-pressure determining means 134. At S9, the control device determines a pulse pressure PP (mmHg), i.e., a difference between the greatest magnitude (a systolic blood pressure) and the smallest magnitude (a diastolic blood pressure) of each heartbeat-synchronous pulse of the carotid pulse wave, in other words, an amplitude of the each heartbeat-synchronous pulse, based on a waveform of the each heartbeat-synchronous pulse of the carotid pulse wave continuously detected by the carotid-pulse-wave sensor 76. The thus determined heart rate HR and pulse pressure PP are stored, in the memory device 106, as the values obtained after the pressing using the cuffs is started, i.e., after the load is applied to the circulatory organ of the subject.

Then, the control goes to S10 corresponding to the first blood-pressure determining means 86 and the second blood-pressure determining means 88. More specifically described, the control device determines an amplitude of each of successive heartbeat-synchronous pulses of the cuff pulse wave represented by the pulse-wave signal $SM_1$ continuously supplied from the pulse-wave filter circuit 36, and determines a right-leg first systolic blood-pressure value $BP1_{RSYS}$, etc. based on the change of the thus determined amplitudes according to well-known oscillometric blood-pressure determining algorithm. Similarly, the control device determines an amplitude of each of successive heartbeat-synchronous pulses of the cuff pulse wave represented by the pulse-wave signal $SM_2$ continuously supplied from the pulse-wave filter circuit 50, and determines a left-leg first systolic blood-pressure value $BP1_{LSYS}$, etc. based on the change of the thus determined amplitudes according to the oscillometric blood-pressure determining algorithm. In addition, the control device determines an amplitude of each of successive heartbeat-synchronous pulses of the cuff pulse wave represented by the pulse-wave signal $SM_3$ continuously supplied from the pulse-wave filter circuit 62, and determines a second systolic blood-pressure value $BP2_{SYS}$, a second diastolic blood-pressure value $BP2_{DIA}$, etc. based on the time-wise change of the thus determined amplitudes according to the oscillometric blood-pressure determining algorithm.

After all the blood-pressure values are determined according to the blood-pressure determining routine at S10, the control goes to S11 corresponding to the cuff-pressure changing means 114. At S11, the control device switches the three switch valves 30, 46, 58 to their quick-deflation positions, so that the respective pressures of the three cuffs 24, 40, 52 are quickly lowered, so that the load applied by the cuffs 24, 40, 52 to the circulatory organ is removed.

Then, the control goes to S12 corresponding to the superior-and-inferior-limb blood-pressure-index determining means 126. At S12, the control device calculates a right-leg index value $ABI_R$ by dividing, by the second systolic blood-pressure value $BP2_{SYS}$ determined at S10, the right-leg first systolic blood-pressure value $PB1_{RSYS}$ also determined at S10, and calculates a left-leg index value $ABI_L$ by dividing, by the second systolic blood-pressure value $BP2_{SYS}$ determined at S10, the left-leg first systolic blood-pressure value $BP1_{LSYS}$ also determined at Step S10. Then, at S13 corresponding to the simultaneous-displaying control means 128 and the timewise-change displaying means 130, the control device controls the display device 70 to display the right-leg index value $ABI_R$ and the left-leg index value $ABI_L$, both determined at S12, and the pulse-wave propagation velocity PWV determined at S7. For example, the control device displays, in a two-dimensional coordinate system that is defined by an ABI axis and a pulse-wave-propagation-velocity axis, and is displayed on an image screen of the display device 70, a symbol at a position defined by the pulse-wave propagation velocity PWV determined at S7 and the lower one of the right-leg index value $ABI_R$ and the left-leg index value $ABI_L$ each determined at S12. The two-dimensional graph includes a boundary between an abnormal range (not greater than 0.9), and a normal range, of the index value ABI that are experimentally determined in advance, and a boundary between an abnormal range (not smaller than 1,000 (cm/sec)), and a normal range, of the pulse-wave propagation velocity PWV that are also experimentally determined in advance, and an area corresponding to the respective abnormal ranges of the index value ABI and the propagation velocity PWV has a color different from that of an area corresponding to the respective normal ranges of the index value ABI and the propagation velocity PWV, so that an operator such as a doctor or a nurse can easily understand the results of measurements. In addition, the display device 70 simultaneously displays, in the two-dimensional coordinate system, not only the symbol corresponding to the current measurement, but also a plurality of symbols corresponding to a plurality of past measurements, so that the operator can observe timewise changes of the index value ABI and the propagation velocity PWV Then, the control goes to S14 corresponding to the variance determining means 136. At S14, the control device utilizes the heart-rate values HR and the pulse-pressure values PP that are iteratively determined at S8 and S9 during a prescribed period of, e.g., from several tens of seconds to several minutes after the pressing of the upper arm 20 with the cuff 52 and the pressing of the ankles 12, 16 with the cuffs 24, 40 under the control of the cuff-pressure changing means 114 are simultaneously started to measure respective blood-pressure values of the upper arm 20 and the ankles 12, 16 and thereby measure an index value ABI. That is, the control device determines a variance $\sigma_{HR}^2$ as a degree of dispersion of those heart-rate values HR, and a variance $\sigma_{PP}^2$ as a degree of dispersion of those pulse-pressure values PP, according to the above-indicated Expressions 2 and 3, respectively. The thus determined variances $\sigma_{HR}^2$, $\sigma_{PP}^2$ are displayed on the display device 70.

Then, the control goes to S15 corresponding to the evaluating means 138. At S15, the control device evaluates a function of the autonomic nerve of the patient, based on the variance $\sigma_{HR}^2$ determined at S14 as the degree of dispersion of the heart-rate values HR, and the variance $\sigma_{PP}^2$ determined at S14 as the degree of dispersion of the pulse-pressure values PP. For example, first, the control device determines an amount or rate of change of the variance $\sigma_{HR}^2$ of the heart-rate values HR measured after the upper arm and the ankles are simultaneously pressed by the cuff-pressure changing means 114, from a variance $\sigma_{HR}^2$ of the heart-rate values HR measured and stored before the upper arm and the ankles are simultaneously pressed, and/or an amount or rate of change of the variance $\sigma_{PP}^2$ of the pulse-pressure values PP measured after the upper arm and the ankles are simultaneously pressed by the cuff-pressure changing means 114, from a variance $\sigma_{PP}^2$ of the pulse-pressure values PP measured and stored before the upper arm and the ankles are simultaneously pressed. Then, the control device judges whether the thus determined amount or rate of change of variance $\sigma_{HR}^2$ of heart-rate values HR is greater than a first pre-set reference value, and whether the thus determined amount or rate of change of variance $\sigma_{PP}^2$ of pulse-pressure values PP is greater than a second pre-set reference value. If the amount or rate of change of variance $\sigma_{HR}^2$ of heart-rate values HR is greater than the first reference value, and/or if the amount or rate of change of variance $\sigma_{PP}^2$ of pulse-pressure values PP is greater than the second reference value, then the control device makes an evaluation that the function of the autonomic nerve is high and normal; and if the amount or rate of change of variance $\sigma_{HR}^2$ of heart-rate values HR is not greater than the first reference value, and if the amount or rate of change of variance $\sigma_{PP}^2$ of pulse-pressure values PP is not greater than the second reference value, then the control device makes an evaluation that the function of the autonomic nerve is low and abnormal, that is, the patient has autonomic imbalance. Then, the control goes to S16 corresponding to the autonomic-nerve-function displaying means 140. At S16, the control device operates the display device 70 to display the result of evaluation made at S15, so that a doctor can easily make a diagnosis on the function of the autonomic nerve of the patient.

It emerges from the foregoing description of the preferred embodiment that the variance determines means (i.e., the dispersion-degree determining means) 136 (S14) determines the variance $\sigma_{HR}^2$ as the degree of dispersion of the heart-rate values HR determined by the heart-rate determining means 132 (S8) after the cuff-pressure changing means 114 (S4 to S6) starts pressing the superior and inferior limbs of the living subject. Since the variance $\sigma_{HR}^2$ as the degree of dispersion of the heart-rate values HR indicates the function or activity of the autonomic nerve of the subject, the function of the autonomic nerve can be easily evaluated or inspected based on the variance $\sigma_{HR}^2$ of the heart-rate values HR, without needing to make the subject take a special resting position or without needing to employ a considerably large-size mechanism for tilting a bed on which the subject rests.

In addition, in the illustrated embodiment, the variance determines means (the dispersion-degree determining means) 136 (S14) also determines the variance $\sigma_{HR}^2$ of the heart-rate values HR measured before the cuff-pressure changing means 114 starts inflating the cuffs 52, 24, 40 to simultaneously press the superior and inferior limbs of the living subject, and the evaluating means 138 (S15) evaluates the function of the autonomic nerve of the subject based on the amount or rate of change of the variance $\sigma_{HR}^2$ of the heart-rate values HR measured before the simultaneous pressing, from the variance $\sigma_{HR}^2$ of the heart-rate values HR measured after the simultaneous pressing. Thus, the activity of the autonomic nerve is evaluated based on the amount or rate of change of the degree of dispersion of the heart-rate values HR measured after the pressing of the superior and inferior limbs of the subject, from the degree of dispersion of the heart-rate values HR measured before the pressing. This evaluation is very accurate because individual differences are removed.

Also, in the illustrated embodiment, the variance determines means (i.e., the dispersion-degree determining means) 136 (S14) determines the variance $\sigma_{PP}^2$ as the degree of dispersion of the pulse-pressure values PP determined by the pulse-pressure determining means 134 (S9) after the cuff-pressure changing means 114 (S4 to S6) starts pressing the superior and inferior limbs of the living subject. Since the variance $\sigma_{PP}^2$ as the degree of dispersion of the pulse-pressure values PP indicates the function or activity of the autonomic nerve of the subject, the function of the autonomic nerve can be easily evaluated based on the variance $\sigma_{PP}^2$ of the pulse-pressure values PP, without needing to make the subject take a special resting position or without needing to employ a considerably large-size mechanism for tilting a bed on which the subject rests.

Also, in the illustrated embodiment, the variance determines means (the dispersion-degree determining means) 136 (S14) also determines the variance $\sigma_{PP}^2$ of the pulse-pressure values PP measured before the cuff-pressure changing means 114 starts inflating the cuffs 52, 24, 40 to simultaneously press the superior and inferior limbs of the living subject, and the evaluating means 138 (S15) evaluates the function of the autonomic nerve of the subject based on the amount or rate of change of the variance $\sigma_{PP}^2$ of the pulse-pressure values PP measured before the simultaneous pressing, from the variance $\sigma_{PP}^2$ of the pulse-pressure values PP measured after the simultaneous pressing. Thus, the activity of the autonomic nerve is evaluated based on the amount or rate of change of the degree of dispersion of the pulse-pressure values PP measured after the pressing of the superior and inferior limbs of the subject, from the degree of dispersion of the pulse-pressure values PP measured before the pressing. This evaluation is very accurate because individual differences are removed.

The illustrated autonomic-nerve-function evaluating apparatus is built in the inferior-and-superior-limb blood-pressure-index measuring apparatus 10, and the simultaneous pressing of the inferior and superior limbs with the cuffs 52, 24, 40 for the measurement of index ABI is also utilized for the evaluation of the function of autonomic nerve. Thus, the present evaluating apparatus enjoys an advantage that it need not employ an exclusive pressing device.

While the present invention has been described in its preferred embodiment by reference to the drawings, it is to be understood that the invention may otherwise be embodied.

For example, in the illustrated embodiment, the pressing to apply load to the circulatory organ of the living subject is effected using the three cuffs 52, 24, 40. However, it is possible to employ a fourth cuff so as to be wound around the other upper arm different from the upper arm around which the cuff 52 is wound, and be inflated to press the other arm. In this case, a greater load is applied to the circulatory organ of the subject and accordingly the reliability of evaluation of the function of the autonomic nerve is improved.

In the illustrated embodiment, the cuffs 24, 40 are wound around the ankles 12, 16, respectively. However, those cuffs may be wound around right and left femoral portions of the living subject, respectively. In this case, a greater load is applied to the circulatory organ of the subject and accordingly the reliability of evaluation of the function of the autonomic nerve is improved.

In the illustrated embodiment, the variances $\sigma_{HR}^2$, $\sigma_{PP}^2$ are determined as the respective degrees of dispersion of the heart-rate values HR and the pulse-pressure values PP. However, respective standard deviations $\sigma_{HR}$, $\sigma_{PP}$, or respective half-value widths, of respective distributions of heart-rate values HR and pulse-pressure values PP may be determined in place of the variances.

In the illustrated embodiment, the variances $\sigma_{HR}^2$, $\sigma_{PP}^2$ are determined as the respective degrees of dispersion of the heart-rate values HR and the pulse-pressure values PP. However, a degree of dispersion of heart-rate values HR and pulse-pressure values PP with respect to a regression line may be determined.

In the illustrated embodiment, the respective degrees of dispersion of the heart-rate values HR and the pulse-pressure values PP measured after the commencement of slow decreasing of the pressures of the cuffs 52, 24, 40, are determined. However, respective degrees of dispersion of heart-rate values HR and pulse-pressure values PP measured after the commencement of increasing of the pressures of the cuffs 52, 24, 40, may be determined.

In the illustrated embodiment, both the variance $\sigma_{HR}^2$ as the degree of dispersion of the heart-rate values HR and the variance $\sigma_{PP}^2$ as the degree of dispersion of the pulse-pressure values PP are determined. However, one of the two variances $\sigma_{HR}^2$, $\sigma_{PP}^2$ may not be determined.

In the illustrated embodiment, the simultaneous pressing of the inferior and superior limbs with the cuffs 52, 24, 40 for the measurement of index ABI is utilized for the evaluation of the function of autonomic nerve. However, it is possible to provide the illustrated autonomic-nerve-function evaluating apparatus, independent of the inferior-and-superior-limb blood-pressure-index measuring apparatus 10.

In the illustrated embodiment, the heart-rate determining means 132 determines the heart-rate values HR based on the respective heartbeat-synchronous pulses of the carotid pulse wave detected by the carotid-pulse-wave sensor 76. However, an electrocardiograph device may be employed, so that the heart-rate determining means 132 may determine heart-rate values HR based on respective heartbeat-synchronous pulses of an electrocardiogram detected by the electrocardiograph device.

In the illustrated embodiment, the carotid-pulse-wave sensor 76 is employed. However, the carotid-pulse-wave sensor 76 may be replaced with a radial-pulse-wave sensor that detects a pressure pulse wave from a radial artery of a living subject and is disclosed in, e.g., PCT Publication No. WO88/4910 or its corresponding U.S. Pat. No. 5,099,853, or Japanese Patent Document TOKU-KAI-HEI No. 2-45033.

It is to be understood that the present invention may be embodied with other changes, improvements and modifications that may occur to a person skilled in the art without departing from the spirit and scope of the invention defined in the appended claims.

What is claimed is:

1. An apparatus for evaluating a function of an autonomic nerve of a living subject, comprising:

a heart-rate measuring device which iteratively measures a heart rate of the subject;

a cuff-pressure changing device which changes a pressure in a first cuff adapted to be wound around an inferior limb of the subject, and a pressure in a second cuff adapted to be wound around a superior limb of the subject, so as to press the inferior and superior limbs; and a dispersion-degree determining means for determining a first degree of dispersion of the heart-rate values iteratively measured by the heart-rate measuring device after the cuff-pressure changing device starts pressing the inferior and superior limbs.

2. An apparatus according to claim 1, wherein the dispersion-degree determining means determines a second degree of dispersion of the heart-rate values iteratively measured by the heart-rate measuring device before the cuff-pressure changing device starts pressing the inferior and superior limbs, and wherein the apparatus further comprises an evaluating means for evaluating the function of the autonomic nerve of the subject based on a change of the first degree of dispersion from the second degree of dispersion.

3. An apparatus according to claim 2, further comprising:

a display device; and an autonomic-nerve-function displaying means for operating the display device to display an evaluation of the function of the autonomic nerve that is made by the evaluating means.

4. An apparatus according to claim 1, wherein the dispersion-degree determining means determines, as the first degree of dispersion, a variance of the heart-rate values iteratively measured by the heart-rate measuring device.

5. An apparatus according to claim 1, further comprising an inferior-and-superior-limb blood-pressure-index measuring device which measures an inferior-and-superior-limb blood-pressure index of the subject.

6. An apparatus according to claim 5, wherein the inferior-and-superior-limb blood-pressure-index measuring device comprises:

an inferior-limb blood-pressure measuring device which measures an inferior-limb blood-pressure value of the inferior limb of the subject;

a superior-limb blood-pressure measuring device which measures a superior-limb blood-pressure value of the superior limb of the subject; and an index determining means for determining the inferior-and-superior-limb blood-pressure index of the subject, based on the inferior-limb blood-pressure value measured by the inferior-limb blood-pressure measuring device and the superior-limb blood-pressure value measured by the superior-limb blood-pressure measuring device.

7. An apparatus according to claim 6, wherein the inferior-limb blood-pressure measuring device comprises the first cuff, the superior-limb blood-pressure measuring device comprises the second cuff, and the inferior-limb blood-pressure measuring device and the superior-limb blood-pressure measuring device commonly comprise the cuff-pressure changing device which changes the pressure in the first cuff and the pressure in the second cuff.

8. An apparatus according to claim 5, further comprising a display device which displays the inferior-and-superior-limb blood-pressure index measured by the inferior-and-superior-limb blood-pressure-index measuring device.

9. An apparatus according to claim 1, further comprising a display device which displays the first degree of dispersion of the heart-rate values that is determined by the dispersion-degree determining means.

10. An apparatus for evaluating a function of an autonomic nerve of a living subject, comprising:

a pulse-pressure measuring device which iteratively measures a pulse pressure of the subject;

a cuff-pressure changing device which changes a pressure in a first cuff adapted to be wound around an inferior limb of the subject, and a pressure in a second cuff adapted to be wound around a superior limb of the subject, so as to press the inferior and superior limbs; and a dispersion-degree determining means for determining a first degree of dispersion of the pulse-pressure values iteratively measured by the pulse-pressure measuring device after the cuff-pressure changing device starts pressing the inferior and superior limbs.

11. An apparatus according to claim 10, wherein the dispersion-degree determining means determines a second degree of dispersion of the pulse-pressure values iteratively measured by the pulse-pressure measuring device before the cuff-pressure changing device starts pressing the inferior and superior limbs, and wherein the apparatus further comprises an evaluating means for evaluating the function of the autonomic nerve of the subject based on a change of the first degree of dispersion from the second degree of dispersion.

12. An apparatus according to claim 11, further comprising:

a display device; and an autonomic-nerve-function displaying means for operating the display device to display an evaluation of the function of the autonomic nerve that is made by the evaluating means.

13. An apparatus according to claim 10, wherein the dispersion-degree determining means determines, as the first degree of dispersion, a variance of the pulse-pressure values iteratively measured by the pulse-pressure measuring device.

14. An apparatus according to claim 10, further comprising an inferior-and-superior-limb blood-pressure-index measuring device which measures an inferior-and-superior-limb blood-pressure index of the subject.

15. An apparatus according to claim 14, wherein the inferior-and-superior-limb blood-pressure-index measuring device comprises:

an inferior-limb blood-pressure measuring device which measures an inferior-limb blood-pressure value of the inferior limb of the subject;

a superior-limb blood-pressure measuring device which measures a superior-limb blood-pressure value of the superior limb of the subject; and an index determining means for determining the inferior-and-superior-limb blood-pressure index of the subject, based on the inferior-limb blood-pressure value measured by the inferior-limb blood-pressure measuring device and the superior-limb blood-pressure value measured by the superior-limb blood-pressure measuring device.

16. An apparatus according to claim 15, wherein the inferior-limb blood-pressure measuring device comprises the first cuff, the superior-limb blood-pressure measuring device comprises the second cuff, and the inferior-limb blood-pressure measuring device and the superior-limb blood-pressure measuring device commonly comprise the cuff-pressure changing device which changes the pressure in the first cuff and the pressure in the second cuff.

17. An apparatus according to claim 14, further comprising a display device which displays the inferior-and-superior-limb blood-pressure index measured by the inferior-and-superior-limb blood-pressure-index measuring device.

18. An apparatus according to claim 10, further comprising a display device which displays the first degree of dispersion of the pulse-pressure values that is determined by the dispersion-degree determining means.

* * * * *